US 6,303,085 B1

(12) United States Patent
Kwak et al.

(10) Patent No.: US 6,303,085 B1
(45) Date of Patent: Oct. 16, 2001

(54) RADICAL GENERATING SYSTEM

(75) Inventors: Shin-Ung Kwak, Inchon; Chong-Man Yoon; Sang-Seon Nam, both of Seoul; Su-Hiang Kang, Inchon; Jong-Yeol Moon, Inchon; Hae-Sang You, Inchon, all of (KR)

(73) Assignee: Daewoo Electronics Co., Ltd., Seoul (KR)

( * ) Notice: Subject to any disclaimer, the term of this patent is extended or adjusted under 35 U.S.C. 154(b) by 0 days.

(21) Appl. No.: 09/474,005

(22) Filed: Dec. 28, 1999

(30) Foreign Application Priority Data

Dec. 28, 1998 (KR) .................................................. 98-59613

(51) Int. Cl.⁷ ........................................................ B01J 19/08
(52) U.S. Cl. ................ 422/186.07; 68/163; 261/DIG. 42
(58) Field of Search ......................... 422/186.07; 68/163; 261/DIG. 42

(56) References Cited

U.S. PATENT DOCUMENTS

| 5,590,551 | 1/1997 | Hong ........................................ 68/183 |
| 5,653,129 | 8/1997 | Jang ........................................ 68/13 R |
| 6,085,556 | * 7/2000 | Moon et al. ........................... 68/13 A |

FOREIGN PATENT DOCUMENTS

| 19740053A1 | 3/1999 | (DE) . |
| 60-153982 | 8/1985 | (JP) . |
| 10-230286 | 9/1998 | (JP) . |

OTHER PUBLICATIONS

PCT International Search Report; Application No. PCT/KR 99/00825; Daewoo Electronics Co., Ltd.; Filed on Dec. 28, 1999.

* cited by examiner

Primary Examiner—Kishor Mayekar
(74) Attorney, Agent, or Firm—Jacobson Holman, PLLC

(57) ABSTRACT

A radical generating system integrates a bubble generating means, an ozone generating means, and a radical changing means. In the radical generating system, the bubble generating means generate air for generating air bubbles and pumping. The ozone generating means applies high voltage to the air bubbles and ozone introduced from the bubble generating means in order to produce ozone. The radical changing means changes the ozone which is introduced from the ozone generating means into a first active oxygen radical. The housing has the bubble generating means, the ozone generating means, and the radical changing means all formed integrally. The radical generating system sterilizes bacilli such as bacteria, viruses, mold, fungi, or algae which live in the water or air. The radical generating system also improves washing effect of a washing machine by oxidizing and bleaching actions of radicals.

13 Claims, 5 Drawing Sheets

RADICAL GENERATING SYSTEM

BACKGROUND OF THE INVENTION

1. Field of the Invention

The present invention relates to a radical generating system, and more particularly, to radical generating system having a bubble generating means, an ozone generating means, and a radical changing means all formed integrally.

2. Prior Art

Most clothes washing machines wash the laundry by using the mechanical force of a pulsator and the surface active force of a chemical detergent. Accordingly, in order to improve the washing efficiency, many clothes washing machine makers have utilized various methods including: improving the pulsator's ability to agitate the laundry, extending the operation time of the motor for water flow time, and improving the quality and/or increasing the quantity of detergent used in the washing machine. However, there are limits to improvements in the washing efficiency by the aforementioned methods for the following reasons. The methods utilizing increased mechanical force to improve the washing efficiency may damage the laundry or decrease efficiency of the clothes washing machine.

In the methods utilizing increased amounts of detergent, a relatively large amount of the detergent which does not react with the laundry is then discharged where it can later cause environmental pollution, and also the remaining detergent sticks to the laundry and thus the laundry is not effectively cleaned.

U.S. Pat. No. 5,653,129, (issued to Byung-Kew Jang on Aug. 5, 1997) discloses a bubble automatic washing machine, which has a bubble generating means and an ozone generating means connected to each other in parallel.

FIG. 1 shows a conventional bubble automatic washing machine 100 with a bubble generating means and an ozone generating means connected to each other in parallel, described in the U.S. Pat. No. 5,653,129.

The washing machine 100 includes a housing 102 and a stationary washer tub 104 fixedly mounted within housing 102 for containing a level of washing fluid therein. Pulsator 106 is rotatable in a forward or reverse direction to create a vortex flow within rotatable tub 112.

The top of washing machine 100 is provided with a door 108 for loading and unloading the laundry articles. Bubble generating means 110 is mounted on the inner surface of door 108 to extend toward rotatable tub 112. Bubble generating means 110 is shown in FIG. 2 in detail. An air pump 116 is communicated with bubble generating means 110 through an air conduit 114. In the drawings, air pump 116 is installed at the bottom plate of washing machine 100 but may be installed at any other suitable place.

Bubble generating means 110 includes a telescopic pipe 202 which is movable upward and downward, and driver 204 for actuating telescopic pipe 202. Though 3-stage telescopic pipe 202 is shown in the drawings, the number of stages is not specially limited as long as the washing machine operates smoothly.

Telescopic pipe 202 is fixed to a casing 218 of driver 204 coaxially with rotatable tub 124. Casing 218 is fixed to the inner surface of door 108 and a DC motor 206 is installed to casing 218. A driving shaft 208 of DC motor 206 is operatively connected to a first pulley 210 which is operatively connected to a second pulley 214 through a belt 212.

Second pulley 214 has a groove for belt 212 and gear teeth formed separately, and a flexible plastic string 216 is wound on the gear teeth. A train of teeth is formed on flexible plastic string 216 to mesh with the gear teeth. Flexible plastic string 216 has a suitable flexibility for being forced to expand and withdraw telescopic pipe 202.

Flexible plastic string 216 extends within, via a hole 219 formed to casing 218, an inner telescopic pipe 220 which is coaxially installed inside the inner telescopic pipe 202 and has the top end fixed to casing 218. The end of flexible plastic string 216 is fixed to the lower end of inner telescopic pipe 220 which is fixed to the lower end of telescopic pipe 202.

The lowest stage of telescopic pipe 202 is provided with a plurality of spurt holes 222 to create air bubbles. Air conduit 114 extends through casing 218 and communicates with inside of telescopic pipe 202. A space between telescopic pipe 202 and inner telescopic pipe 220 serves as an air passage and the air flowing out of air conduit 114 blows into rotatable tub 112, sequentially passing through the space and spurt holes 222.

An ozone generating means 118 may be further installed between air pump 116 and driver 204 in order to kill bacteria inhabiting the laundry articles. As a result, ozone is contained in air bubbles blowing into rotatable tub 124 to remove bacteria from the laundry articles.

Moreover, a heater 120 may be installed between ozone generating means 118 and driver 204 in order to create a hot air stream for drying the laundry articles. The air stream generated from air pump 116 flows through air conduit 114 to heater 120 to heat up and is transmitted to the laundry articles within rotatable tub 112.

However, a conventional bubble automatic washing machine with the bubble generating means and the ozone generating means connected to each other in paralled has drawbacks,e.g., installation space is occupies a large area and oxygen($O_2$) through the bubble generating means has low degree of generating efficiency of an ozone. In order to get force of washing and cleaning for proper washing is a large amount of ozone is indispensable as well. As a result, induced ozone has the disadvantage of inflict bodily harm due to the high concentration and bad odor of ozone itself.

SUMMARY OF THE INVENTION

Therefore, it is an object of the present invention, for the purpose of solving the above mentioned problems, to provide a radical generating system which integrates a bubble generating means, an ozone generating means, and a radical changing means.

In order to attain the object, according to the present invention, there is provided a radical generating system comprising a housing with a gas mixing chamber disposed therein; a bubble generating means disposed in the housing for pumping air into the gas mixing chamber in order to develop compressed air in the gas mixing chamber; an ozone generating means disposed in the gas mixing chamber for generating ozone from the compressed air; and a radical changing means disposed in the housing and in communication with the gas mixing chamber for changing the ozone received from the gas mixing chamber into active oxygen. The radical changing means includes a catalyst chamber having a hollow, a first side wall having an inlet for allowing the ozone to be introduced from the gas mixing chamber to the catalyst chamber, and a second side wall having an outlet for the active oxygen. An active oxygen generation catalyst is stored in the hollow for catalyzing the change of the ozone into the active oxygen.

Other objects and further features of the present invention will become apparent from the detailed description when read in conjunction with the attached drawings.

BRIEF DESCRIPTION OF THE DRAWINGS

Other features and advantages of the present invention will become more apparent from the following description taken in connection with the accompanying drawings, wherein.

DETAILED DESCRIPTION OF THE PREFERRED EMBODIMENT

The preferred embodiment of the present invention will hereinafter be described in detail with reference to the accompanying drawings.

Figure 1:
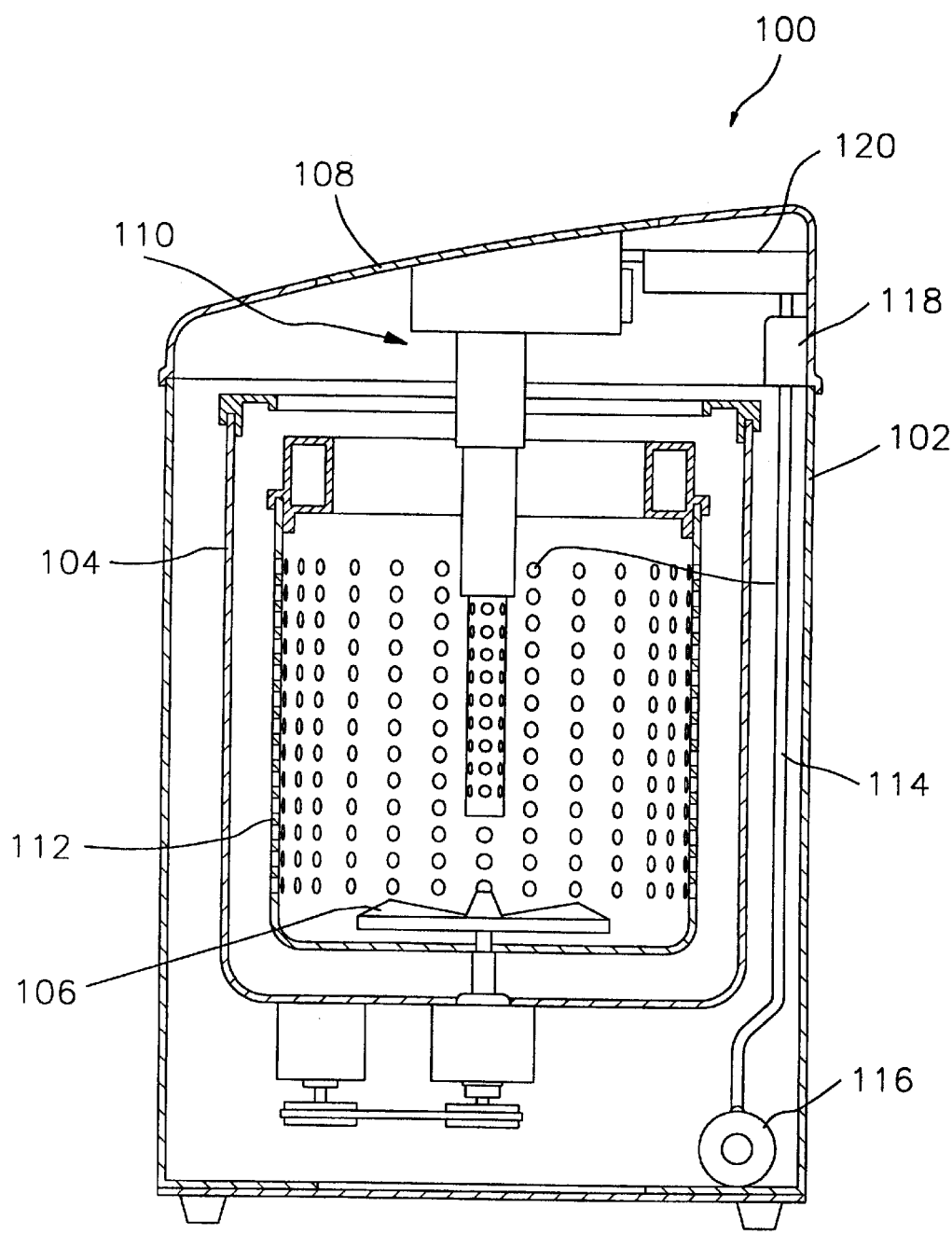
FIG. 1 is a schematic sectional view for showing a conventional bubble washing machine having bubble and ozone generating means connected to each other in parallel.
Figure 2:
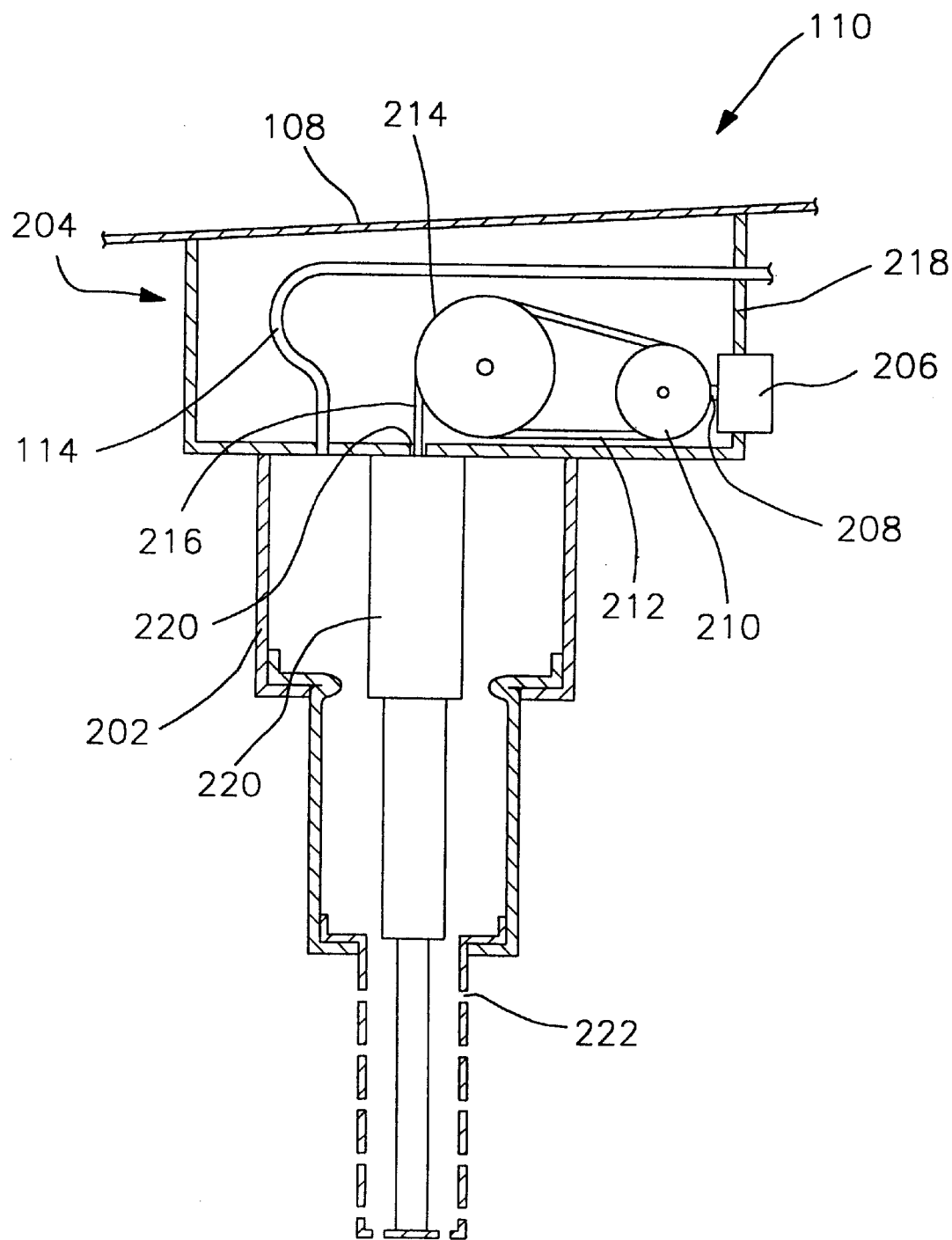
FIG. 2 is an enlarged sectional view of the bubble generating means shown in FIG. 1.
Figure 3:
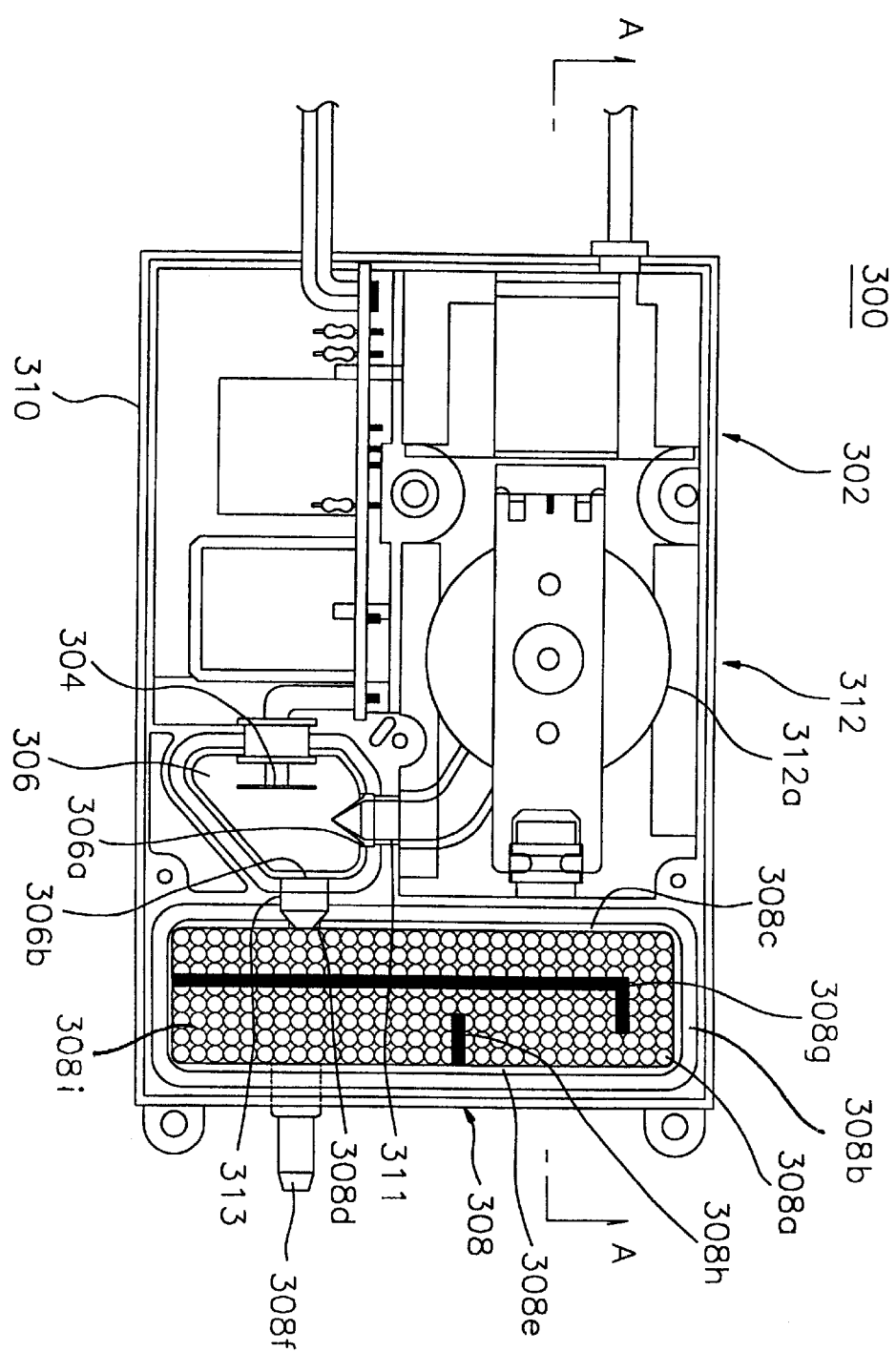
FIG. 3 is a plan view for showing a radical generating system according to a preferred embodiment of the present invention.

FIG. 3 shows a radical generating system 300 according to a preferred embodiment of the present invention. The radical generating system 300 includes a bubble generating means 302, an ozone generating means 304, a radical changing means 308, a housing 310, a first check valve 311, and a second check valve 313.

Figure 4:
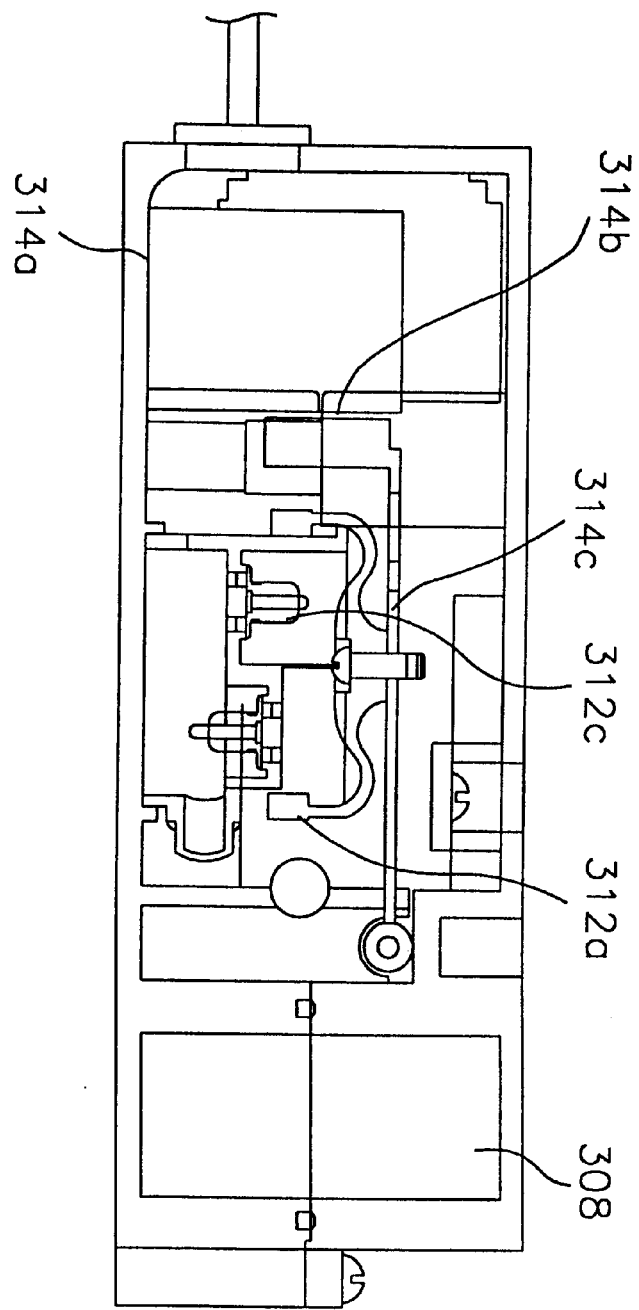
FIG. 4 is a side end view of the bubble generating means taken along line A—A shown in FIG. 3.
Figure 5:
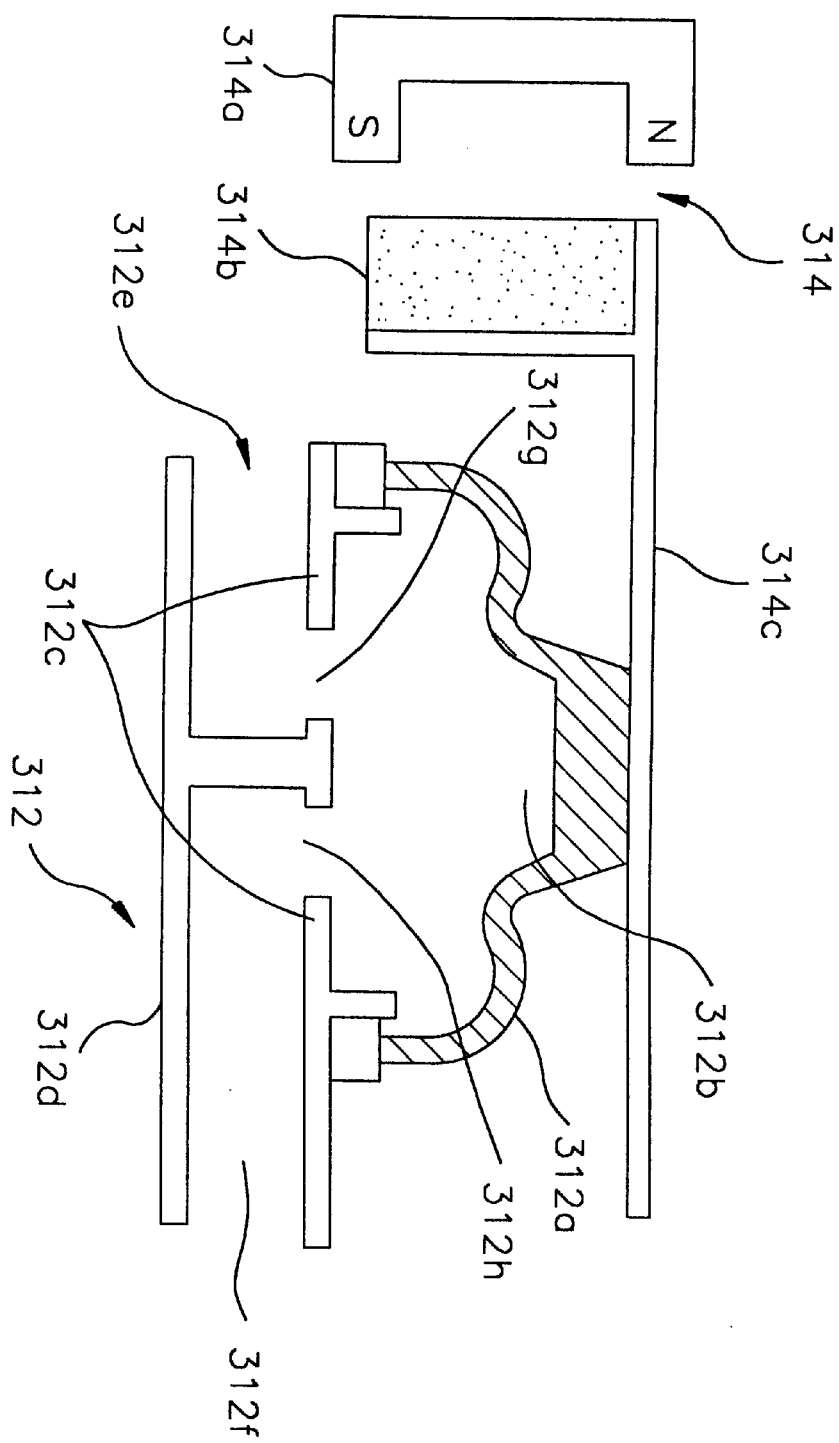
FIG. 5 is a view for illustrating a principle of an operation of the bubble generating means shown in FIGS. 3 and 4.

FIG. 4 is a side end View of the bubble generating means 302 taken along line A—A shown in FIG. 3. FIG. 5 illustrates a principle of an operation of the bubble generating means 302 shown in FIGS. 3 and 4.

The bubble generating means 302 generates air for generating air bubbles. The bubble generating means 302 includes an air pump 312 and an operating section 314. The air pump 312 pumps the air for generating air bubbles and ozone.

The air pump 312 includes a diaphragm 312$a$ fixed to the operating section 314. The diaphragm 312$a$ expands by means of up and down motion of the operating section 314 and expands and contracts volume of a pump chamber 312$b$ formed therein. The diaphragm 312$a$ is formed with a resilient material such as rubber capable of contracting or expanding by an external force. An air pump body 312$d$ is installed apart from valve sheet 312$c$ at a predetermined distance. The air pump body 312$d$ includes an air inlet 312$e$ for introducing external air to the pump chamber 312$b$ by compression and contraction of the diaphragm 312$a$. The air pump body 312$d$ includes an air outlet 312$f$ for discharging the air in the pump chamber 312$b$ to the gas mixing chamber 306. The air introduced through the air inlet 312$e$ is guided into the pump chamber 312$b$ which is defined by the diaphragm 312$a$ and the air pump body 312$d$ through a first hole 312$g$. The air compressed in the pump chamber 312$b$ is discharged to the air outlet 312$f$ through a second hole 312$h$.

The operating section 314 compresses and returns the air pump 312 according to current supply. The operating section 314 includes an electromagnet 314$a$, a magnet 314$b$, and an operating member 314$c$. The electromagnet 314$a$ generates magnetic field according to current supply. The magnet 314$b$ vibrates according to the magnetic field generated by the electromagnet 314$a$. The operating member 314$c$ moves up and down according to the vibration of the magnet 314$b$.

As shown in FIG. 5, the bubble generating means 302 uses a principle of the electromagnet 314$a$. When 100~250V/50~60 Hz power is applied to a coil-wound core, a phase of the electromagnet 314$a$ changes thereby changing polarity of the magnetic field generated around surface of the core. Accordingly, the phenomenon which pushes and pulls the magnet 314$b$ repeats and oscillates sixty times per second. The magnet 314$b$ which oscillates at 10 Hz compresses and returns the air pump 312 so that the pumping operation is performed through the diaphragm 312$a$.

The ozone generating means 304 applies a high voltage to the air pumped by the air pump 312 to generate ozone. The ozone is a triatomic allotrope of oxygen in which the ozone molecule consists of three oxygen atoms in contrast to the two oxygen atoms of the typical oxygen molecule. Ozone can be generated by passing air or oxygen through a high intensity electric field.

The radical changing means 308 is disposed in the housing 302 and communicates with the gas mixing chamber 306. The radical changing means 308 has an active oxygen radical generating catalyst for changing the ozone to active oxygen (—O—, —O$^-$, $^1_gO_2$, and $O_2^{31}$, etc.) generate radicals (—OH—, —OH$^-$, HO$_2$—, HO$_2^-$, H$_2$O$_2$, etc.) when the active oxygens react to water molecules. The radicals comprise the strongest hydroxyl (OH—) radical.

The radical changing means 308 comprises an active oxygen radical generation catalyst 308$a$, and a catalyst chamber 308$b$. The active oxygen radical generation catalyst 308$a$ includes a main catalyst, a sub catalyst, and a catalyst support. The main catalyst has one of TiO$_2$, MnO$_2$, and CuO$_2$. The sub catalyst has either Pt, or Pd. The catalyst support has one of Al$_2$O$_3$, SiO$_2$, and MgO.

The catalyst chamber 308$b$ comprises a hollow 308$i$, a left side wall 308$c$, and a right side wall 308$e$. The hollow 308$i$ forms a hexahedron. The left side wall 308$c$ has inlet 306$a$ for receiving ozone generated by the ozone generating means 304 in the gas mixing chamber 306. The right side wall 308$e$ has outlet 306$b$ through which the active oxygens are discharged from the radical changing means 308. The catalyst chamber 308$b$ further comprises a first separate membrane 308$g$ and a second separate membrane 308$h$. The first separate membrane 308$g$ is installed at the inner surface of the hollow 308$i$ between the ozone inlet 308$d$ and the radical outlet 308$f$. The second separate membrane 308$h$ is installed at the inner surface of the hollow 308$i$ between the first separate membrane 308$g$ and the radical outlet 308$i$.

The housing 310 has the bubble generating means 302, the ozone generating means 304, and the radical changing means 308 all formed integrally.

The first check valve 311 is mounted between the bubble generating means 302 and the gas mixing chamber 306. The first check valve 311 selectively introduces the air from the bubble generating means 302 to the ozone generating means 304. The first check valve 311 serves to prevent the supply of air from the bubble generating means 302 from flowing inversely.

The second check valve 313 is mounted between the gas mixing chamber 306 and the radical changing means 308. The second check valve 313 selectively introduces the air for generating air bubbles from the ozone generating means 304 to the radical changing means 308. The second check valve 313 serves to prevent the supply of air for generating air bubbles from the ozone generating means 304 from flowing inversely.

Hereinafter, an operation of the radical generating system 300 according to a preferred embodiment of the present invention will be described.

When current is applied to the electromagnet 314a of operating section 314 of the bubble generating means 302, the electromagnet 314a generates a magnetic field. The magnet 314b vibrates according to the magnetic field generated by the electromagnet 314a. The operating member 314c moves up and down according to the vibration of the magnet 314b.

The diaphragm 312a of air pump 312 expands by means of up and down motion of the operating member 314c and expands and contracts volume of a pump chamber 312b formed therein to thereby pump the air for generating air bubbles.

The first check valve 311 injects the air for generating air bubbles from the bubble generating means 302 to the gas mixing chamber 306 so that the gas mixing chamber 306 stores the air. The ozone generating means 304 applies the high voltage to the air in the gas mixing chamber 306 in order to produce ozone.

The second check valve 313 injects the mixed air and ozone in the gas mixing chamber 306 into the radical changing means 308. The ozone is decomposed into the active oxygen by an active oxygen radical generating catalyst 308a which is included in the radical changing means 308. The ozone then goes past the first separate membrane 308g and the second separate membrane 308h in sequence. As contact time and flow distance of the ozone is extended, the ozone forms a vortex and the radical changing means 308 improves i:he generating efficiency of the ozone.

The strong oxidizing action of the first-series active oxygen radical and the second-series active oxygen radical effectively sterilizes bacilli such as bacteria, viruses, mold, fungi, or algae which live in the air, water, and solid material. That is, the radicals attack protoplasm membrane of a fungus and it is sterilized by the lysis.

A deodorizing process for the radicals is differs from chemical conversion process according to induction material of the odors. But radicals of aromatic compounds, for example, break C=C bond so that induction ingredient of the odors convert the molecular structure to become odorless.

Effects of the radical generating system according to the present invention as constructed above will be described below.

The radical generating system according to the present invention sterilizes bacilli such as bacteria, viruses, mold, fungi, or algae which live in washing water or clothes. The present invention also improves washing effect of a washing machine by oxidizing and bleaching actions of the first-series active oxygen radical and the second-series active oxygen radical.

The radical generating system has a sterilizing/deodorizing effect to prevent a reduction the sterilizing efficiency and environmental pollution by the additive ingredient such as a solid material which is maintained based on the application time of the ingredient having oxide power. The radical generating system has a high degree of efficient sterilization and deodorization in comparison with the ozone generating means, so no unpleasant odor nor harm occurs.

A radical generating system of the present invention can be applied a various fields and products such cleaning beds, water purifier, sewage purification, drainage treatment, washing machine, refrigerator, humidifier, and cleaning machine, etc.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A radical generating system comprising:
   a housing;
   a gas mixing chamber disposed in the housing;
   bubble generating means disposed in the housing for pumping air into the gas mixing chamber in order to develop a compressed air in the gas mixing chamber;
   ozone generating means disposed in the gas mixing chamber for generating ozone from the compressed air; and
   radical changing means disposed in the housing and in communication with the gas mixing chamber for changing the ozone which is introduced from the gas mixing chamber into an active oxygen, said radical changing means including
      a catalyst chamber having a hollow formed as a hexahedron, a first side wall having an inlet for allowing the ozone to be introduced to the catalyst chamber, and a second side wall having an outlet for the active oxygen; and
      an active oxygen radical generation catalyst stored in the hollow for catalyzing the change of the ozone into the active oxygen.

2. The radical generating system according to claim 1, wherein the active oxygen radical generation catalyst comprises:
   a main catalyst having one of $TiO_2$, $MnO_2$, and $CuO_2$;
   a sub catalyst having either Pt or Pd; and
   a catalyst support having one of $Al_2O_3$, $SiO_2$, and MgO.

3. The radical generating system according to claim 1, wherein the catalyst chamber further comprises:
   a first separate membrane installed at an inner surface of the hollow between the ozone inlet and the outlet; and
   a second separate membrane installed at an inner surface of the hollow between the first separate membrane and the outlet.

4. The radical generating system according to claim 1, wherein the active oxygen is changed into a hydroxyl radical when the active oxygen reacts to water.

5. The radical generating system according to claim 1, wherein the ozone generating means applies a high voltage to the compressed air for generating the ozone.

6. A washing machine comprising:
   a housing;
   a gas mixing chamber disposed in the housing;
   bubble generating means disposed in the housing for pumping air into the gas mixing chamber in order to develop a compressed air in the gas mixing chamber;
   ozone generating means disposed in the gas mixing chamber for generating ozone; and
   radical changing means disposed in the housing and in communication with the gas mixing chamber for changing the ozone into an active oxygen, wherein the radical changing means includes
      a catalyst chamber having a hollow, a first side wall having an inlet for allowing the ozone to be introduced from the gas mixing chamber to the hollow, and a second side wall having an outlet for allowing the active oxygen to be discharged from the hollow to an exterior; and an active oxygen radical generation catalyst stored in the hollow for changing the ozone into the active oxygen, the active oxygen radical generating catalyst comprising a main catalyst having one of $TiO_2$, $MnO_2$, and $CuO_2$, a sub catalyst having either Pt or Pd, and a catalyst support having one of $Al_2O_3$, $SiO_2$, and MgO.

7. The radical generating system according to claim 6 wherein the ozone generating means applies a high voltage to the compressed air in the gas mixing chamber to generate the ozone.

8. A radical generating system comprising:

a housing with a gas mixing; chamber disposed therein;

bubble generating means disposed in the housing for pumping air into the gas mixing chamber in order to develop a compressed air in the gas mixing chamber;

ozone generating means disposed in the gas mixing chamber; and radical changing means disposed in the housing and in communication with the gas mixing chamber for changing ozone which is introduced from the gas mixing chamber into an active oxygen, said radical changing means including a catalyst chamber having an inlet for allowing ozone to be introduced and an outlet for discharge of the active oxygen; and an active oxygen radical generation catalyst for catalyzing the change of the ozone into the active oxygen.

9. The radical generating system according to claim 8, wherein the radical generating system is a washing machine.

10. The radical generating system according to claim 8 wherein the active oxygen radical generation catalyst comprises:

a main catalyst having one of $TiO_2$, $MnO_2$, and $CuO_2$;

a sub catalyst having either Pt or Pd; and a catalyst support having one of $Al_2O_3$, $SiO_2$, and MgO.

11. The radical generating system according to claim 8 wherein the catalyst chamber further comprises:

a first separate membrane installed at an inner surface of the chamber between the inlet and the outlet; and a second separate membrane installed at an inner surface of the chamber between the first separate membrane and the outlet.

12. The radical generating system according to claim 8, wherein the active oxygen is changed into a hydroxyl radical when the active oxygen reacts to water.

13. The radical generating system according to claim 8, wherein the ozone generating means applies a high voltage to the compressed air in the gas mixing chamber to generate the ozone.

* * * * *